United States Patent [19]

Phillips et al.

[11] 4,276,023
[45] Jun. 30, 1981

[54] FLUID FLOW CONTROL CONSOLE

[75] Inventors: Earl G. Phillips, Kalamazoo Township, Kalamazoo County; Dee B. Ranger, Oshtemo Township, Kalamazoo County, both of Mich.

[73] Assignee: Stryker Corporation, Kalamazoo, Mich.

[21] Appl. No.: 79,869

[22] Filed: Sep. 28, 1979

[51] Int. Cl.³ .......................... A61C 1/10; A61C 1/12; A61C 1/02; A61M 1/00
[52] U.S. Cl. ........................................ 433/85; 433/82; 433/100; 128/276
[58] Field of Search ..................... 433/82, 28, 100, 85; 128/66, 276; 137/DIG. 8; 251/25, 26

[56] References Cited

U.S. PATENT DOCUMENTS

| 747,493 | 12/1903 | Scruggs | 285/320 |
|---|---|---|---|
| 2,449,497 | 9/1948 | McLeod | 128/276 |
| 2,985,469 | 5/1961 | Bowman, Jr. | 285/304 |
| 3,065,749 | 11/1962 | Brass | 128/276 |
| 3,208,145 | 9/1965 | Turner | 128/276 |
| 3,469,582 | 9/1969 | Jackson | 128/276 |
| 3,568,318 | 3/1971 | Martin | 433/100 |
| 3,610,242 | 10/1971 | Sheridan | 128/276 |
| 3,749,090 | 7/1973 | Stewart | 128/240 |
| 3,889,675 | 6/1975 | Stewart | 128/240 |
| 3,964,484 | 6/1976 | Reynolds et al. | 128/276 |
| 3,986,262 | 10/1976 | Casillas | 433/28 |
| 3,993,054 | 11/1976 | Newman | 128/66 |
| 4,049,000 | 9/1977 | Williams | 128/276 |
| 4,075,761 | 2/1978 | Behne et al. | 433/85 |
| 4,182,038 | 1/1980 | Fleer | 433/85 |

Primary Examiner—Gene Mancene
Assistant Examiner—Michael J. Foycik
Attorney, Agent, or Firm—Blanchard, Flynn, Thiel, Boutell & Tanis

[57] ABSTRACT

A fluid control for powering and supplying coolant liquid to gas operated surgical and dental tools and for supplying irrigant to a suction-irrigation handpiece, selectively by remove control from a surgical or dental operating site. A console remote from the operating site has a pressurized gas source. The tool and an operator valve actuable for turning on the tool are located at the operating site, remote from the console. A tool gas supply at the console is actuable for supplying pressurized gas from the source to the remote operator valve and tool. A coolant supply at the console is actuable for delivering coolant liquid to an outlet tip located at the tool. Gas circuitry in the console responds to the drop in gas pressure in the tool gas supply resulting from turning on of the tool and thereby causes the coolant supply to supply liquid to the tip while the tool is running. A low pressure gas tube connects from the console to the handpiece and operator controlled means on the handpiece control flow and this pressure therein. An irrigant supply in the console is actuable for supplying irrigant liquid to the handpiece at the operating site. Further gas circuitry responds to a change in pressure in the low pressure gas tube to cause the liquid supply to supply irrigant liquid to the handpiece.

13 Claims, 5 Drawing Figures

FLUID FLOW CONTROL CONSOLE

FIELD OF THE INVENTION

This invention relates to apparatus for supplying coolant and/or irrigant liquids to a surgical or dental operating site as well as to apparatus for controlling operation of gas operated surgical or dental tools and suction handpiece devices usable at such an operating site.

BACKGROUND OF THE INVENTION

Surgical and dental procedures, including for example orthopedic surgery, ENT/neurosurgery, trauma surgery and oral surgery, as well as other, frequently require use, by the doctor or nurse or other assistant, of various gas or liquid handling devices at the operating site, or wound.

Such devices include various pressurized gas operated tools for cutting, boring, etc, which are normally gas operated rather than electrically operated to avoid electric shock and explosion hazards. Other devices are used to supply liquid to the operating site, for example to cool the bur or cutter of the tool, to irrigate the wound for removal of debris and clots or to otherwise clean the wound, as well as for other purposes. In addition, suction devices are frequently employed to remove unwanted material from the wound, such as excess irrigation liquid, blood, and other flowable debris.

In some instances it may be necessary or desirable to employ all of these devices at a single operating site, or wound. This has raised certain difficulties in the past. For example, it has been common in the past to use liquid supply devices, for irrigation or tool bit cooling, in the form of refillable bulb syringes. Typically, the operating nurse is constantly filling and refilling bulb syringes and passing them to the surgeon. This raises the risk of contamination due to multiple pass offs and the lack of a closed fluid pathway and the difficulty in calculating or recording the amount of liquid used in irrigation and retrieved in suction. On the other hand, the surgeon carrying out the procedure may be faced with the need to simultaneously control the tool, coolant flow, irrigation flow and suction, aside from the need to control placement of the various devices with respect to the wound. Thus the surgeon may have to rely on other to handle at least some of these devices, with attendant inaccuracy in timing and placement, an excessive number of hands in a crowded surgical field, and an excessive number of devices, tubes, hoses and support items at the operating site. Moreover, the use of bulb syringes as a source of cooling or irrigant liquid deprives the doctor of the option of pulsed, steady rate or drip irrigation.

Accordingly, the objects and purposes of the invention include provision of:

A fluid flow control system permitting simultaneously two-handed control of cutting or boring tool operation, cutter coolant liquid flow, pulsed or other type irrigation flow, and suction, permitting the surgeon to himself handle all of these functions simultaneously.

A system, as aforesaid, in which sensing of gas pressures at a console remote from the operating site controls delivery of irrigant and coolant liquid to the operating site and in which the liquid supply path is in each instance through a continuous and unbroken tube from supply container to operating site to minimize risk of contamination.

A system, as aforesaid, in which all liquid supply and debris retrieving devices and tubing are disposable.

A system, as aforesaid, in which all pneumatic and electrical control circuitry is disposed in a console remote from the operating site and no electrical wiring extends to the operating site.

Other objects and purposes of this invention will be apparent to persons acquainted with apparatus of this general type upon reading the following specification and inspecting the accompanying drawings.

SUMMARY OF THE INVENTION

The objects and purposes of the invention are met by providing a surgical and dental fluid control system for supplying liquid to a hand-held device, or devices, at a surgical or dental operating site. A console is positionable remotely from the operating site. A pressurized gas source and a liquid source are provided at the console. Elongated tubes supply gas at a desired pressure from the console to the device at the operating site. The device has means actuable by a person at the operating site for changing the gas flow rate in the gas supply tube. Means at the console respond to change in pressure in the tube due to such actuation, for initiating flow of the liquid to the device at the operating site. A further tube interposed between the liquid source and the device at the operating site carries out the supplying of liquid to the operating site.

DETAILED DESCRIPTION

Figures 1, 1A, 1B:
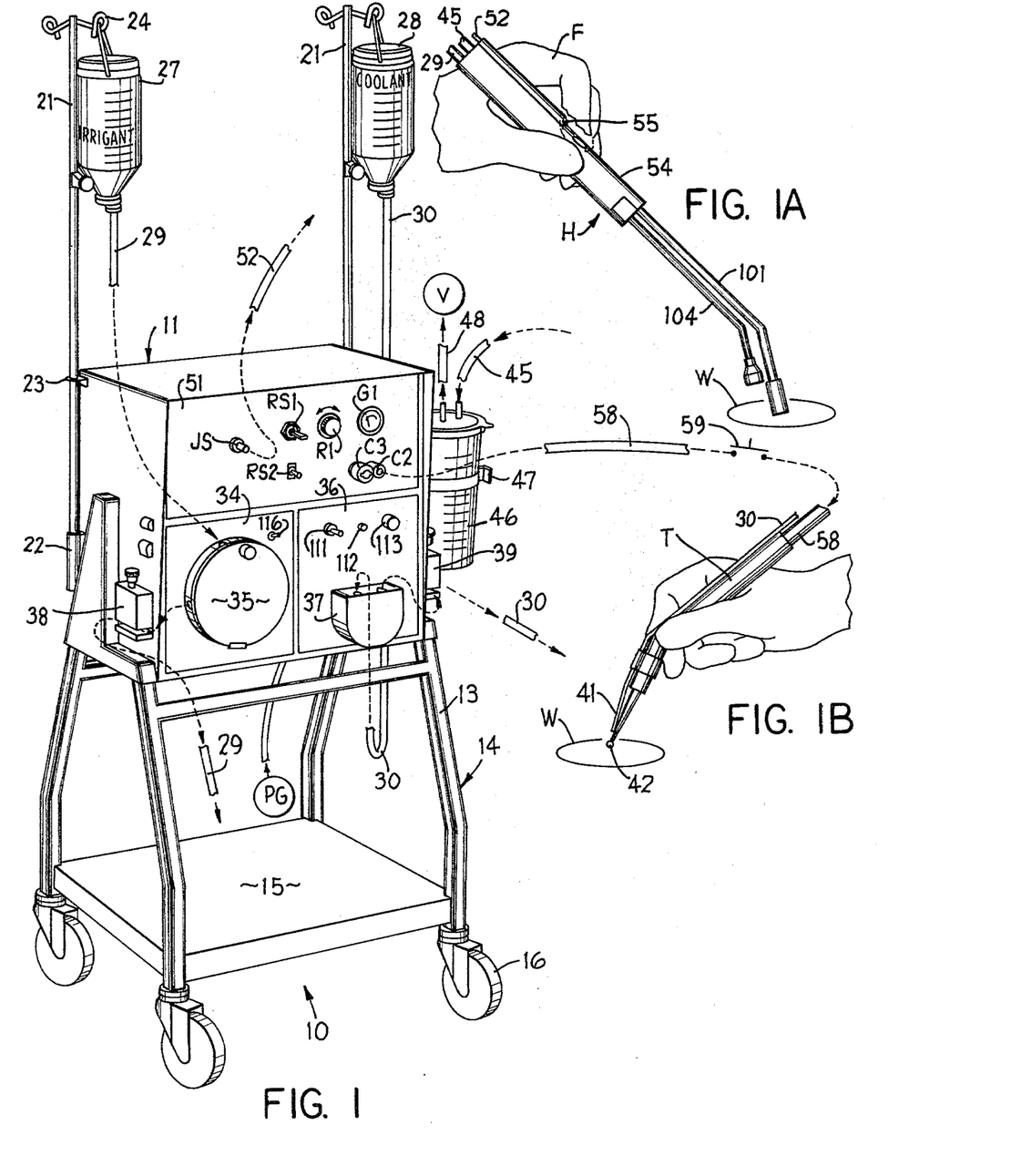
FIG. 1 is a pictorial view of a fluid-flow control console embodying the invention.
FIG. 1A is an enlarged pictorial view of a suction-irrigation handpiece connectible to the console of FIG. 1 for use at a remote operating site.
FIG. 1B is an enlarged pictorial view of a rotary surgical tool and coolant tip connectible to the console of FIG. 1 for use at a remote operating site.

FIG. 1 discloses a fluid-flow control console 10 embodying the invention. The console 10 includes a rectangular control cabinet 11 fixed atop a base 14, having a shelf 15 and legs 13 supported on casters 16.

A pair of upstanding posts 21 are each removably fixed by brackets 22 and 23 to the cabinet 11. Hooks 24 at the upper ends of the posts 21 pendently support clear, graduated liquid containers 27 and 28, which feed depending, flexibly clear plastic tubes 29 and 30. The containers 27 and 28 conveniently are conventional I.V. bottles or flexible pouches. The containers 27 and 28 supply irrigant liquid and tool coolant liquid as hereinafter discussed. Elevation of the containers 27 and 28 above the level of the operating site, where a surgical or dental procedure is to be carried out, permits gravity feeding of either liquid to a device at the operating site. An operating site, or wound is generally indicated at W in FIGS. 1A and 1B.

The console 10 in the disclosed embodiment includes a pulsed output pump 34 and a continuous output pump 36, arranged in the cabinet 10 as interchangeable modules, such that the pumps 34 and 36 can be interchanged with each other or for entirely different pump modules, as a particular dental or surgical procedure may require. To prevent contamination of the liquids therein, the tubes 29 and 30 are preferably unbroken between their supply containers 27 and 28 and the devices at the operating site which they are to supply. Accordingly, pumps 34 and 36 are preferably flexible tube pumps, or peristaltic pumps, capable of forcing liquid through tubes 29 and 30 by pinching same while advancing the point of pinching forwardly therealong, in a conventional manner. The pumps include electric drive motors, energized as hereafter described.

The pump 34 is preferably of the kind disclosed in U.S. Pat. No. 3,993,054, assigned to the assignee of the present invention. The flexible tube 29 from the irrigant liquid source 27 is led, as indicated by broken line arrows, through the pump (past the pump roller, not shown), through an I.V. clamp 38 and then to the operating site, for example to the irrigant liquid inlet of a suction irrigation handpiece H (FIG. 1A). The I.V. clamp 38 is spring biased closed to pinch the tube 29 to block flow therethrough. A hinged faceplate 35 on the pump 34 opens for quick installation or removal of the tube 29.

The pump 36 is preferably a conventional, continuous feed, peristaltic pump. The flexible tube 30 from the coolant container 28 is led, as indicated by the broken line arrows, through the perstaltic pump 36 (behind the faceplate 37 thereof), through a further I.V. clamp 39 to the operating site, for example to a coolant tip 41 supported on a pneumatic tool T adjacent its working member, e.g., a rotary burr, 42. The clamp 39 is preferably identical to the clamp 38 and similarly is normally spring biased closed.

The console 10 further provides for suction of unwanted material, such as blood, irrigant or coolant liquids, or the like, from the operating site through a flexible suction tube 45 leading from a suction handpiece (as at H in FIG. 1A) at the operating site, to a clear graduated receiving container 46 conveniently secured by a clip 47 to the cabinet 11. The receiving container 46 has a vacuum-tight cover and connects through a further flexible tube 48 to any convenient vacuum supply V, such as to a vacuum pump or to a central vacuum system through a wall socket of the type normally found in hospital operating rooms.

The operating room nurse can easily monitor the quantity of liquids supplied to and removed from the wound during a dental or surgical procedure by noting the change in liquid levels with respect to the graduations on the containers 27, 28 and 46.

Figure 2:
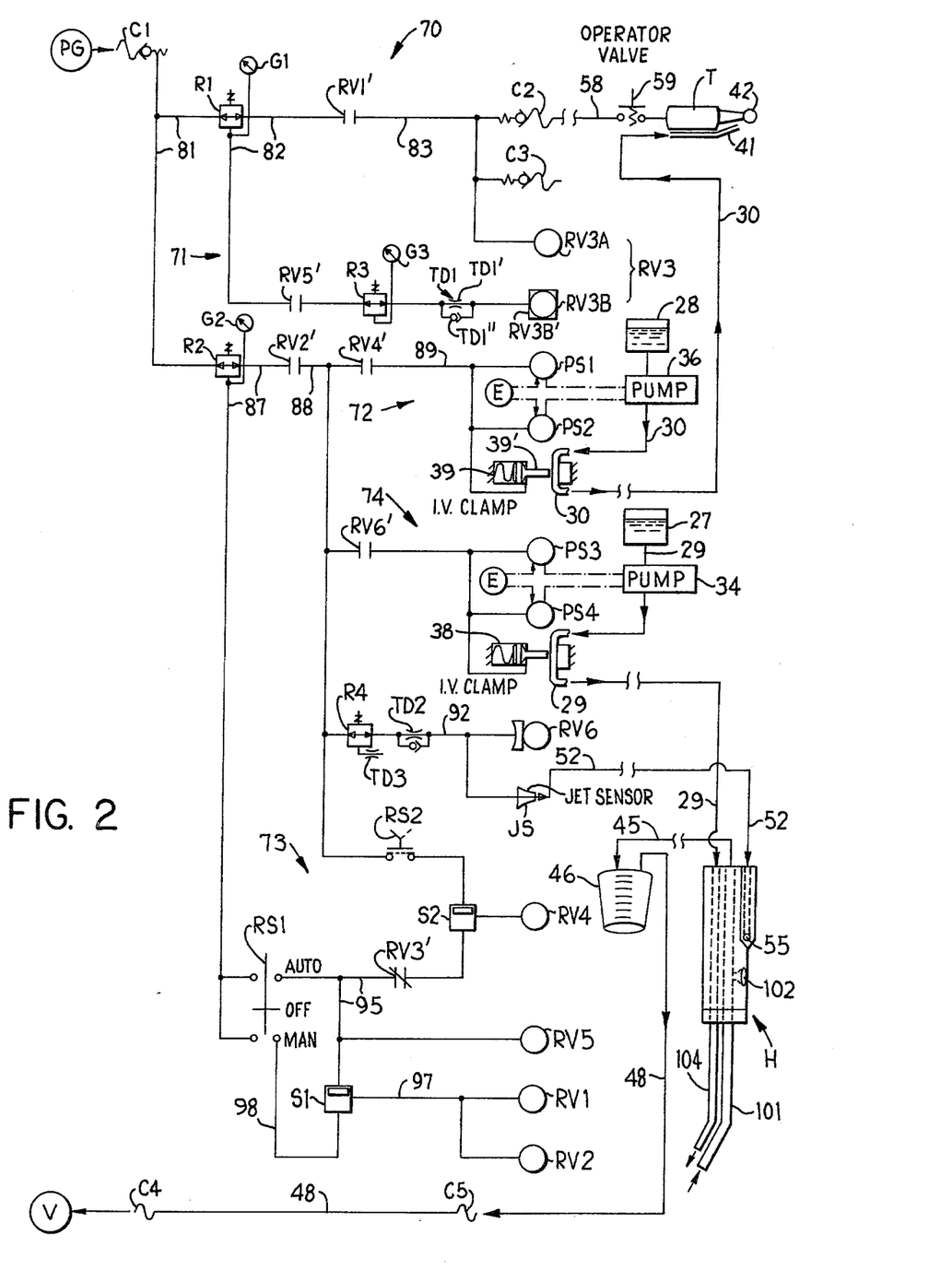
FIG. 2 is a schematic view of pneumatic circuitry of the console of FIG. 1, showing the connection thereto of devices of the kind shown in FIGS. 1A and 1B.
Figure 3:
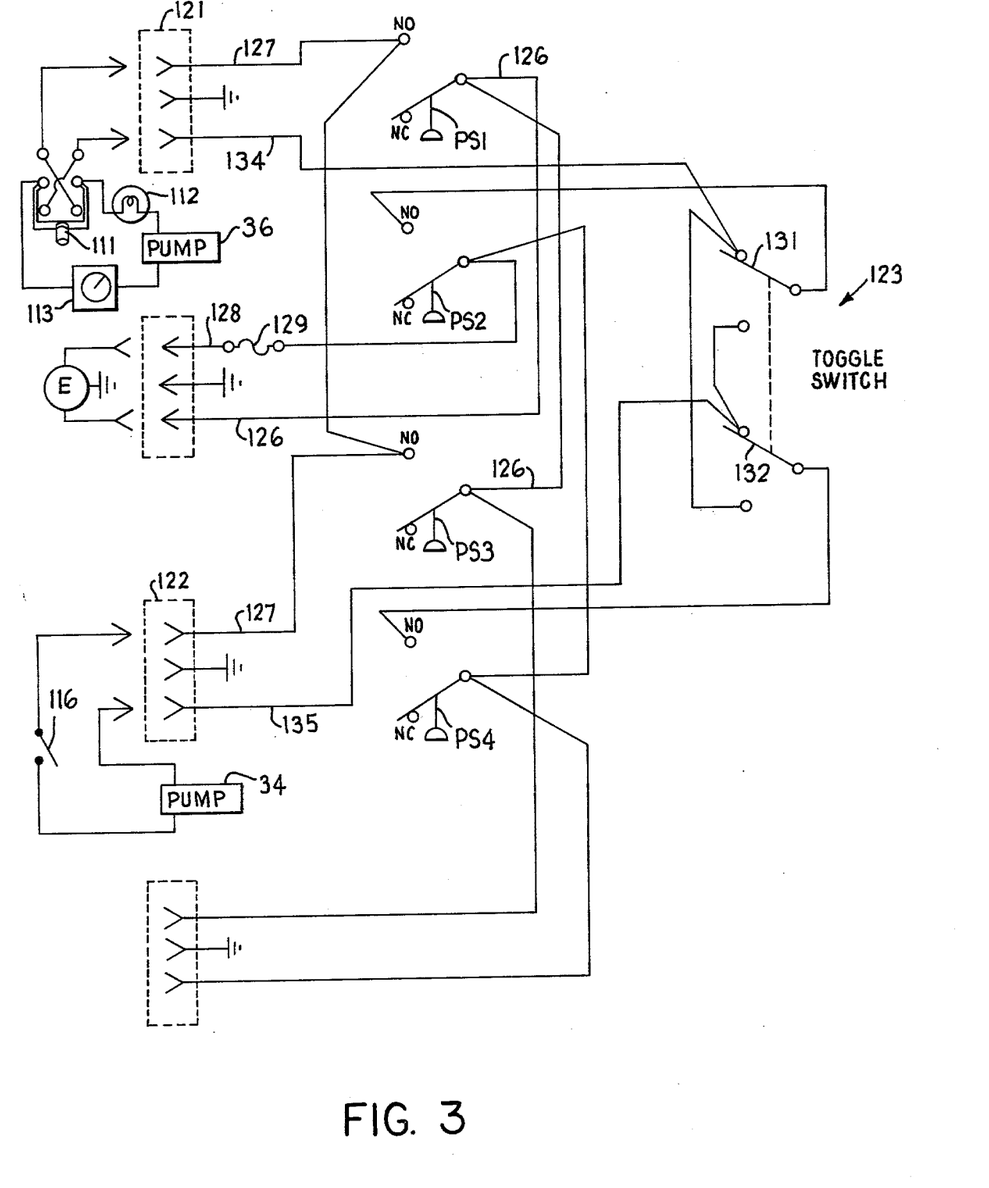
FIG. 3 is a schematic diagram of electrical circuitry of the console of FIG. 1.

The cabinet 11 also houses pneumatic and electrical control circuitry hereafter described with respect to FIGS. 2 and 3 and housed behind a front panel 51 (FIG. 1). The panel 51 supports a low pressure gas outlet JS releasably connected through a flexible tube 52 to supply low pressure gas at a low flow rate to the suction irrigation handpiece H of FIG. 1A to remotely control the irrigant pump and I.V. clamp as hereafter described. Accordingly, the handpiece H is preferably of the type disclosed in copending U.S. application Ser. No. 79,870, filed Sept. 28, 1979, assigned to the assignee of the present invention and the disclosure of which is incorporated by reference herein. Such handpiece includes a handle 54 provided with an opening 55 communicating with low pressure gas tube 52 and closable by the finger F of the operator to signal the console 10 to supply irrigant liquid through tube 29 to the handpiece.

The cabinet front panel 51 also carries high pressure gas outlets C2 and C3 alternatively selectable for energizing the pneumatic tool T of FIG. 1B.

Additional control system components accessible on the outside of cabinet 11 are discussed hereafter with respect to FIGS. 2 and 3.

Applicant's pneumatic control circuit 70 (FIG. 2) is housed in cabinet 11. The pneumatic circuit 70 is powered by a conventional pressurized gas source PG. As hereafter discussed, some gas from source PG may be released at the operating site. Thus, the source PG is preferably a nitrogen gas source, such as a storage tank under pressure or a compressor. Gas from the source PG is applied to the circuit 70 through a conventional connector incorporating a check valve C1.

The circuit 70 includes a portion 71 for pneumatically driving the tool T and further includes portions 72 and 73 actuable, to flow of coolant liquid to the coolant tip 41, either manually of in automatic response to energization of the tool T. A further portion 74 of circuitry 70 controls the flow of irrigant liquid to the handpiece H in response to manual control of the opening 55 in the handpiece.

The interconnection of the individual elements of the pneumatic circuit 70 is clearly shown in FIG. 2 and such circuit elements are identified in the following discussion of the operation of pneumaic circuit 70.

The source PG supplies gas at a pressure exceeding that required by all pressure fluid devices fed by the circuit 70. The highest pressure will normally be demanded by the tool T, typically at some rated pressure level in the range of 80 to 160 pounds per square inch (psi), hereafter termed the tool actuating pressure. Gas at above tool actuating pressure from gas source PG passes through a line 81 to a manually settable pressure regulator R1. The regulator R1 and its outlet pressure gauge G1 appear on the front panel 51 of cabinet 11 (FIG. 1) and the tool operator or his assistant (e.g. doctor or nurse) normally pre-adjusts the regulator R1 to the tool actuating pressure for the particular tool T to be used, for example 100 psi. The regulator R1 applies gas at such pressure through lines 82 to normally blocked, pilot actuated valves RV1' and RV5'. Thus, the tool supply and sensing portion 71 of the circuit remains unactuated.

The gas pressure of source PG is also applied through line 81 to a further pressure regulator R2, the output pressure of which is monitored by a gauge G2. Regulator R2 is normally preset by the manufacturer of the console 10 at a desired level for actuating circuit portions 72, 73 and 74, for example at 80 psi, hereafter referred to as the circuitry pressure. Regulator R2 and gauge G2 are normally contained within the cabinet 11. The output of regulator R2 is applied to lines 87. One line 87 is normally blocked by a pilot actuated valve RV2'. The other line 87 leads to the input side of a manual-off-automatic valve RS1 which appears on the front panel 51 (FIG. 1) and is manually actuable to any one of its three positions. Valve RS1 is normally in its off position shown and so blocks gas flow from line 87 therepast. Actuation of the remainder of circuit 70 thus will not take place until valve RS1 is manually shifted to either its automatic or manual position.

Attention is first directed to operation upon manual shifting of valve RS1 to its upper, automatic position. Such applies gas at circuitry pressure through a valve output line 95 direct to a valve pilot RV5 which unblocks aforementioned pilot actuated valve RV5' in circuitry portion 71. Accordingly, gas at tool actuating pressure is applied from line 82 through valve RV5' to a third pressure regulator R3. The pressure regulator R3, and its output pressure gauge G3, are not seen in FIG. 1 but are normally provided on the back of cabinet 11, and accessible to the operator for setup purposes. Setup is accomplished by the operator setting regulator R3 at an output pressure less than that at which he has set regulator R1, by a preselected differential recommended by the manufacturer (e.g. 25 psi). Accordingly, with the regulator R1 set at 100 psi, the regulator R3 might be set at 75 psi, hereafter referred to as the reference pressure. Gas at the reference pressure passes from regulator R3 through a one-way time delay unit TD1 to the reference pilot RV3B of a dual pilot valve unit RV3. The valve unit RV3 is a conventional dual pilot valve having gas actuated, oppositely acting pilots, one of which is additionally spring biased as hereafter discussed. The time delay unit TD1 is a conventional one-way time delay oriented to delay actuation of reference pilot RV3B for a predetermined time after unblocking of valve RV5' (due to the flow restrictor portion TD1' thereof), while permitting free return flow of gas from reference pilot RV3B leftwardly without delay (by passage through the open check valve portion TD1'' thereof).

Returning now to the time of shifting valve RS1 to its automatic position, the pressurized gas in line 95 also passes through a shuttle valve S1 and a line 97 to energize further valve pilots RV1 and RV2. The shuttle valve S1 is a conventional shuttle valve containing a shuttle member S1' which blocks gas flow between the upper and lower ends of valve S1 but permits gas flow to the line 97 from either the upper or lower end of shuttle valve S1.

Such actuation of pilot RV2 unblocks normally blocked pilot actuated valve RV2', to supply gas at circuitry pressure from regulator R2 through a line 88 to circuitry portions 72 and 74 hereinafter discussed.

On the other hand, the actuation of valve pilot RV1 unblocks pilot actuated valve RV1' and thereby applies gas at the tool actuating pressure from regulator R1 through a line 83 to check valve equipped outlet fittings C2 and C3 appearing on the front panel 51 of cabinet 11. The outlet fittings C2 and C3 are conventional fittings in which the check valve portion normally blocks egress of gas therethrough from line 83. A conventional complimentary fitting (not shown) on the end of tool supply tube 58 plugs into the fitting C2 to open the check valve portion of fitting C2 and permit gas flow from the line 83 into the tool supply tube 58. In the particular embodiment shown, the fitting C3 is of a different style than fitting C2 and is provided to adapt the console 10 to tools having a differently shaped tubing inlet fitting.

Interposed in the tube 58 adjacent the tool T, for example as a hand operated device incorporated in the tool T itself or as a foot operated device operable by a doctor or nurse adjacent the operating site, there is provided a normally blocking valve 59 manually actuable to pass pressurized gas to, and operate, the tool T.

Thus, with tube 58 plugged into fitting C2, the above-mentioned unblocking of pilot actuated valve RV1' provides gas under tool actuating pressure to the operator controlled valve 59 remote from the console 10, for actuating tool T and thereby rotating its burr or cutting bit 42. The tool T can be de-energized by blocking valve 59 or unplugging tube 58 from check valve fitting C2.

The aforementioned unblocking of pilot actuated valve RV1' and pressurizing of line 83 also pressurizes the tool sensing pilot RV3A of the dual pilot unit RV3.

To review timing, the aforementioned shifting of valve RS1 from "off" to "automatic" pressurizes pilot RV3A before pilot RV3B, since pressurizing of the latter is delayed by the time delay device TD1' above discussed. Note that prior to shifting of valve RS1 out of its off position, valve RV3' is blocked. Shifting of valve RS1 to "automatic" acts first to apply (through valve RV1') full tool actuating pressure to pilot RV3A which maintains the valve RV3' blocked. The subsequent delayed actuation of the other pilot RV3B (through valve RV5' and time delay TD1') cannot overcome the fully pressurized pilot RV3A. Thus, it will be seen that the time delay TD1' insures that "blocking" pilot RV3A takes control of valve RV3' before "unblocking" pilot RV3B has a chance to do so.

In this state of the circuit, operator actuation of remote tool valve 59 applies gas to the tool to rotate burr 42. Gas consumption by the rotating tool T drops the pressure at the blocking pilot RV3A enough to allow the unblocking pilot RV3B (which is still at reference pressure) to overcome the blocking pilot RV3A and thereby unblock the valve RV3'. In the embodiment shown, pilot RV3B is spring assisted, the spring being schematically indicated by the square box RV3B' around the circular pilot symbol, such spring assisting the reference gas pressure in the aforementioned overcoming of the blocking pilot RV3A.

In this way, operating the tool T unblocks the pilot valve RV3'. That applies circuit pressure through shuttle valve S2 (preferably identical to shuttle valve S1 above-described) to energize a valve pilot RV4, which immediately unblocks its contact RV4' and thereby applies gas at circuit pressure through the line 89 to the circuit portion 72. The thus pressurized line 89 immediately closes two pressure operated electrical switches PS1 and PS2 to complete both legs of an electrical circuit (schematically shown in chain line in FIG. 2) through a conventional electrical source E and electric motor of the desired pump, here the continuous output pump 36. This causes the pump 36 to run. At the same time, said unblocking of valve RV4' also pressurizes the IV clamp 39 to retract the spring-backed piston 39' thereof and thereby permit the energized pump 36 to move coolant from container 28 therepast through line 30 out the coolant tip 41 to cool the working member 42.

However, when the operator turns off the tool T, by permitting valve 59 to return to its normal blocked condition, pressure in the line 83 again rises to full tool actuating pressure, so that tool sensing pilot RV3A again overcomes reference pilot RV3B and blocks pilot valve RV3'. Accordingly, the valve RV4' blocks, pressure is lost in line 89, pressure switches PS1 and PS2 open to de-energize pump 36, and tube 30 is once again clamped shut by IV clamp 39 to block coolant flow to tip 41.

Thus, in the automatic position of switch RS1, pneumatic circuit 70 supplies coolant liquid to tip 41 when and only when tool T is energized.

The operator may wish to flow coolant from tip 41 without turning on the tool T, for example to wash out the operating site thoroughly before use of the tool or after an extensive period of use of the tool. To do so, the operator uses a correspondingly numbered control on front panel 51 to shift a bypass valve RS2 from its normal blocked condition to an unblocked condition. This applies gas at circuit pressure from line 88 through bypass valve RS2 to the upper side of shuttle valve S2, and thereby again pressurizing valve pilot RV4, unblocking valve RV4', actuating coolant pump 36 and unclamping IV clamp 39 to again supply coolant liquid to the tip 41 at the operating site. Coolant liquid then continues to run regardless of the operative state of tool T, until bypass valve R2 is manually returned to its normal blocked condition by the operator.

On the other hand, the operator may wish to run the tool T without having liquid supplied at the tip 41. To do so, the operator shifts manual-automatic valve RS1 downward to its manual position in which gas at circuitry pressure is furnished from line 87 through valve RS1 to a line 98 and thence through shuttle valve S1 to line 97. This leaves line 95 and pilot RV5 unpressurized, so that pilot RV3B cannot control pump 36 and clamp 31, but supplies pressure to pilots RV1 and RV2 above discussed. Thus, valve RV1' is unblocked to permit tool T to be turned on and off by the operator by manipulation of tool valve 59. With the manual-automatic valve RS1 in its manual position for dry running of tool T, the operator can, of course, manually cause coolant liquid to be supplied at tip 41, by manually unblocking bypass valve RS2 in the manner above-discussed. At the same time, valve RV2' is unblocked and maintains circuitry gas pressure on line 88 to enable the irrigation supply for the suction-irrigation handpiece H. Thus, irrigation-suction portion 74 is enabled by circuitry gas pressure on line 88 when valve RS1 is in either its manual or automatic position, though not in its off position.

With line 88 thus pressurized and circuit portion 74 energized, the operator may turn on and off the flow of irrigant liquid to a suction/irrigation handpiece of the type disclosed in aforementioned U.S. Application Ser. No. 79,870, filed Sept. 28, 1979, in the following manner. With the handpiece H connected to the console 10 through irrigant tube 29, vacuum tube 45 and low pressure control tube 52, suction is applied to suction tip 101 of handpiece H by manual covering of a suction relief opening 102 in the handpiece, such that flowable material from the operating site is drawn through the handpiece, tube 45 and into container 46 by the subatmospheric pressure in line 48.

With irrigant circuit portion 74 enabled, the relatively high circuitry pressure (e.g., 80 psi) in line 88 is very substantially stepped down by a very low pressure regulator R4, capable of operating in the range of 0 to 10 psi. Normally regulator R4 is preset at a value in the range of 1 to 3 psi. Low pressure gas flow from restrictor R4 is applied through a time delay device TD2, of the general type above described at TD1, and is then applied to a line 92 leading respectively to a low pressure sensing pilot RV6 and the outlet fixture JS (termed the jet sensor) to which the low pressure tube 52 connects. With the hole 55 in the handpiece H uncovered, gas freely flows through line 92, the jet sensor JS and tube 52 out of hole 55 in the handpiece. Due to low pressure established by regulator R4 and the restriction of flow by delay device TD2, the free gas flow out of hole 55 is so low as to be virtually unnoticeable by the operator holding the handpiece. Thus the flow out of open hole 55 does not tend to distract the operator from performing the dental or surgical procedure. The free flow of gas from line 92 through the handpiece H lowers the pressure on pilot RV6 substantially to 0 psi above atmospheric (i.e., substantially to atmospheric pressure) such that the pilot is unactivated. This leaves the corresponding pilot actuated valve RV6' blocked as shown in FIG. 2. A parallel outlet of regulator R4 through a flow restricted TD3 helps to limit transient pressure changes at the output of regulator R4, and thereby avoid false operation of low pressure pilot RV6.

To cause irrigant flow, the operator blocks handpiece hole 55 and flow through jet sensor JS. Pressure rapidly builds up in line 92 toward the value at the output of regulator R4 (e.g., 1 to 3 psi) so that pilot RV6 is actuated and unblocks its valve RV6'. This supplies gas at circuit pressure (e.g., 80 psi) to pressure actuated electrical switches PS3 and PS4 which close an electrical circuit path (indicated in chain lines in FIG. 2) through a suitable electrical source and the pulsating pump 34 to turn on such pump. Simultaneously, the gas pressure applied to unblock valve RV6' backs the piston of IV clamp 38 against its restoring spring and opens the tube 29 to pumped flow of irrigant liquid from container 27 and pump 34 to handpiece H and out an irrigant tip 104 thereof. Thus, pump 34 and IV clamp 38 respond to unblocking of valve RV6' in substantially the same manner as above discribed pump 36 and IV clamp 39 respond to opening of valve RV4'.

In FIG. 1, continuous flow pump unit 36 is shown as incorporating a forward-off-reverse switch 111, a power on indicator lamp 112 and a speed control 113, all of a conventional nature and indicated schematically in FIG. 3 as being interposed between the pump 36 and a plug-in electrical receptacle 121. Similarly, the pump unit 34 shown in FIG. 1 includes a manual on-off switch 116 shown schematically in FIG. 3 as interposed in circuitry between the pump 34 and a further electrical receptacle 122.

FIG. 3 shows a toggle switch 123 of double pole, double throw type, interposed between the pressure switches and receptacles 121 or 122 to which the pump units connect. Toggle switch 123 is actuable to electrically interchange the pumps 34 and 36, so that pressure switch PS2 will control the pulsating output pump 34 and pressure switch PS4 will control the constant output pump 36. By then switching the tubes 30 and 29 between the pumps, so that pump 36 drives tube 29 and pump 34 drives tube 30, a pulsating coolant flow can be provided to tip 41 and a constant irrigant flow can be applied to handpiece H.

More particularly, a first line 126 from electrical supply E connects through the pressure switches PS1 and PS3 (when closed) and a line 127, to one side of both pump receptacles 121 and 122. The other output line 128 of electrical supply E is fused at 129 and connects through pressure switches PS2 and PS4 (when closed) to the shiftable contacts 131 and 132 of switch 123. In their FIG. 3 position, such contacts 131 and 132 respectively connect pressure switches PS2 and PS4 to the remaining sides 134 and 135 of pump receptacles 121 and 122, for respectively controlling pumps 36 and 34. In the alternate position, not shown, of the contacts 131 or 132 of the switch 123, pressure switches PS2 and PS4 are respectively connected instead to lines 135 and 134, and hence to receptacles 122 and 121 associated with pumps 34 and 36, the connection of pressure switches PS2 and PS4 thus being reversed with respect to pumps 34 and 36.

While operation of jet sensor JS and pilot RV6 has been described above in connection with a supply of gas at a few psi above atmospheric pressure, it is possible to modify the jet sensor circuitry to work with a reversed gas flow direction (away from rather than toward handpiece 8) by use of a gas pressure source which is a few psi below atmospheric pressure, rather than a few psi above atmospheric pressure as in the preferred embodiment of FIG. 2. In such a modified system, pilot RV6 would be replaced with a new pilot actuable in response to a change from substantially atmospheric pressure to a pressure a few psi below atmospheric pressure and regulator RV4 and its connection to line 88 would be replaced by a correspondingly regulated vacuum supply device, wherein such regulation is to avoid spurious variations in the pressure at the new vacuum sensing pilot due to changing conditions in the suction tip 101 and tube 45 of the handpiece.

While pumps 34 and 36 have been disclosed as electrically powered, it is contemplated that pressure fluid operated pumps may instead be used, with a gas inlet replacing the corresponding pressure switch pair PS1, PS2 and PS3, PS4, either for direct supply of pressurized gas from valves RV4' and RV6', or more preferably by using the gas supply from valves RV4' and RV6' to control pilots (not shown) feeding gas from a suitable high capacity supply to such pumps.

The handpiece H is preferably provided with means for reducing irrigant flow, as disclosed in aforementioned copending application Ser. No. 079,870, filed Sept. 29, 1979. This, with slowing of the pump 34 or 36 delivering irrigant liquid to the handpiece, or mere gravity feed of irrigant liquid from container 27 to the handpiece, around the pump, permits very slow, e.g., drip, feeding of irrigant liquid to the handpiece.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a surgical and dental fluid control system for supplying liquid to a handheld pressurized gas operated tool at a surgical or dental operating site, the combination comprising:
   a console remote from said operating site;
   a gas pressure source and a liquid source at said console;
   liquid tube means interposed between said liquid source and said tool at said operating site for carrying said liquid to said operating site;
   elongated gas tube means for supplying gas at a desired pressure from said console to said tool at said operating site, said tool having means manually actuable at the operating site for changing the gas flow rate in said tube means;
   means at said console responsive to a change in flow rate or gas pressure in said gas tube means due to such manual actuation, for initiating a flow of said liquid to said tool at said operating site, said change responsive means including means normally blocking liquid flow from said liquid source through said liquid tube means to said operating site and a gas circuit means for comparing the gas pressure in said gas tube means with a reference value and unblocking said liquid tube blocking means when said gas pressure flow is below said reference value due to tool operation, said gas circuit means comprising a dual pilot valve unit including a sensing pilot connected to said gas tube means and responsive to a drop in gas pressure therein caused by operation of said tool, said dual pilot valve unit having a reference pilot and pressure reducing regulator means interposed between said reference pilot and said gas pressure source for maintaining said reference pilot at a reference pressure at a fixed level below the gas pressure in said gas tube means with said tool turned off, said dual pilot valve unit further including a valve and means responsive to actuation of said valve for unblocking said liquid tube blocking means, said sensing and reference pilots being connected in opposition to said lastmentioned valve for actuation thereof by said reference pilot upon dropping of the pressure applied to said sensing pilot due to turning on of said tool.

2. The apparatus of claim 1 including a manually actuable function selecting valve interposed between said gas pressure source and said valve of said dual pilot valve unit and having an off position blocking application of gas pressure to said valve of said dual pilot valve unit and an automatic position connecting said gas pressure source to said valve of said dual pilot valve unit to enable same.

3. The apparatus of claim 2 including a reference supply pilot, a tool supply pilot, and a clamp supply pilot connected in parallel to said valve of said dual pilot unit to receive gas pressure from said function selecting valve in its automatic position, and reference supply, tool supply and clamp supply valves normally blocked for preventing application of gas pressure to said regulator means, to said tool and sensing pilot, and to said means normally blocking liquid flow, respectively, said function selecting valve having an alternately selectable manual position and including a shuttle valve responsive to selection of said manual position for applying gas pressure from said function selecting valve to said tool supply and clamp supply pilots but not to said reference supply pilot and said valve of said dual pilot unit so as to preclude unblocking of said means normally blocking liquid flow upon turning on of said tool, so as to permit dry running of the tool.

4. The apparatus of claim 2 including a bypass valve manually actuable for applying gas pressure to said means normally blocking liquid flow, to unblock same independent of tool actuation.

5. In a surgical and dental fluid control system for supplying liquid to a hand-held device at a surgical or dental operating site, the combination comprising:
   a console remote from said operating site;
   a gas pressure source and a liquid source at said console;
   liquid tube means interposed between said liquid source and said device at said operating site for carrying said liquid to said operating site;
   elongated gas tube means for supplying gas at a desired pressure from said console to said device at said operating site, said device having means manually actuable at the operating site for changing the gas flow rate in said tube means;
   means at said console responsive to a change in flow rate or gas pressure in said gas tube means due to such manual actuation, for initiating a flow of said liquid to said device at said operating site, said liquid tube means terminating in a tip adjacent the working end of said device for supplying a liquid thereto, said change responsive means including means normally blocking liquid flow from said liquid source through said liquid tube means to said operating site and a gas circuit means for comparing the gas pressure in said gas tube means with a reference value and unblocking said liquid tube blocking means when said gas pressure flow is below said reference value due to tool operation, in which said means normally blocking liquid flow includes a normally deactuated pump and a normally blocking clamp connected in series along said liquid tube means between said liquid source and tip, said gas circuit means for comparing including a valve actuable to apply gas under pressure to pump energizing and clamp de-energizing means to effect pumping of liquid from said source through said clamp to said tip.

6. In a surgical and dental fluid control system for supplying liquid to a hand-held suction-irrigation handpiece at a surgical or dental operating site, the combination comprising:

a console remote from said operating site;

a gas pressure source and a liquid source at said console;

liquid tube means interposed between said liquid source and said handpiece at said operating site for carrying said liquid to said operating site;

elongated gas tube means for supplying gas at a desired pressure from said console to said handpiece at said operating site, said handpiece having means manually actuable at the operating site for changing the gas flow rate in said tube means;

means at said console responsive to a change in flow rate or gas pressure in said gas tube means due to such manual actuation, for initiating a flow of said liquid to said handpiece at said operating site, in which said gas pressure source is a low pressure source near but not equal to atmospheric pressure, said manually actuable means being a relief opening for venting said gas tube means at said handpiece, and normally holding said gas tube means substantially at atmospheric pressure, said liquid tube means communicating with a tip at the working end of said handpiece for supplying irrigant liquid thereto, said gas pressure change responsive means including means normally blocking liquid flow from said source through said liquid tube means to said operating site and a gas circuit for unblocking said tube blocking means when said gas pressure in said gas tube means is restored to the pressure at said low pressure gas source by blocking of said relief hole.

7. The apparatus of claim 6 in which said low pressure gas source includes a pressure regulator presettable to a pressure in the range of 0 to 10 psi above atmospheric pressure, said gas circuit including a time delay device connecting the output of said regulator to said gas tube means, and a pilot connected with said time delay device and the console end of said gas tube means, said means normally blocking liquid flow comprising a pump and tube clamp interposed along said gas tube means between said liquid source and said handpiece, and a valve actuable in response to actuation of said pilot for energizing said pump and unclamping said clamp to effect liquid flow to said handpiece tip.

8. In a surgical and dental fluid control system for powering and supplying coolant liquid to gas operated surgical and dental tools and for supplying irrigant liquid to a suction-irrigation handpiece, selectively by remote control from a surgical or dental operating site, the combination comprising:

a console;

a pressurized gas source at said console, an operator valve actuable by the tool operator for turning on said tool, said tool and operator valve being at the operating site and remote from said console;

tool supply means connected to said gas source and actuable for supplying pressurized gas to said remote operator valve of said tool;

means actuable for supplying a coolant liquid to an outlet tip located at said tool;

means responsive to a drop in gas pressure at said tool supply means resulting from turning on said tool, for supplying coolant liquid from said coolant liquid supply means to said tip at said tool;

means effecting a low pressure gas connection to said handpiece and operator controlled means at said handpiece for controlling flow in said low pressure gas connection;

means for supplying an irrigant liquid to said handpiece at the operating site;

means responsive to a change in pressure in said low pressure gas connection due to operator manipulation of said operator controlled means at said handpiece for actuating said source of irrigant liquid and thereby supplying irrigant liquid to said handpiece.

9. The apparatus of claim 8 in which said coolant liquid supplying means comprises coolant tube means extending from a source of coolant liquid to said tip at said tool, and a normally de-energized continuous flow pump interposed in said coolant tube means, said irrigant liquid supply means including an irrigant tube means connected from an irrigant liquid source to said handpiece, and a normally deactuated pulsating pump interposed in said irrigant tube means, said means responsive to turning on of said tool including as pressure circuit means terminating in first pressure switch means, said means responsive to a change in pressure in said low pressure gas connection including gas circuitry terminating in second pressure switch means, an electrical source responsive to actuation of said first pressure switch means for energizing said continuous flow pump and responsive to actuation of said second pressure switch means for energizing said pulsating pump, electric switch means interposed between said electrical source and first and second pressure switch means for interchanging the connections of said pumps to said first and second pressure switch means, and said tube means being interchangeable between said pumps, for providing pulsed coolant flow to said tip of said tool and continuous irrigant flow to said handpiece.

10. The apparatus of claim 1 including a time delay means interposed between said regulator means and said reference pilot for delaying actuation of said reference pilot until after full actuation of said sensing pilot, upon connection thereto of said gas pressure source, so as to prevent passage of gas through said valve of said dual pilot unit in the absence of gas usage by said tool.

11. The apparatus of claim 5 including a first said pump and blocking clamp and a second said pump and blocking clamp, said first and second pumps having different liquid flow output characteristics, said liquid tube means being switchable between the outlets of said first and second pumps, and including means for correspondingly switching said pump energizing means between said first and second pumps to thereby change the liquid flow characteristic to said tip.

12. In a surgical and dental fluid control system for selectively supplying fluid using tool and handpiece devices at an operating site, by control at said site of fluid sources at a common location remote from said site, the combination comprising:

a console at said common remote location;

elongate tube means extending in parallel from said console to said tool and handpiece devices at said operating site;

means at said console responsive to actuation of a tool control at said operating site for supplying powering pressure fluid from a source at said console through one said tube means to power a tool device at said operating site;

means at said console responsive to said supplying of said powering pressure fluid to said one tube means for automatically supplying coolant liquid from a source at said console through second said tube means to cool said tool device;

means at said console, independent of said tool control and said supplying of powering pressure fluid, and instead responsive to modulation at said operating site of a sensing fluid flow in a third said tube means, for supplying of irrigant liquid from a source at said console, through a fourth said tube means to a handpiece device at said operating site.

13. In a surgical and dental fluid control system for supplying liquid to a hand-held tool at a surgical or dental operating site, the combination comprising:

a console remote from said operating site;

a fluid pressure source at said console;

means responsive to tool actuation for supplying pressure fluid from said console through a tube to power said tool;

tube means for supplying liquid from said console to a liquid outlet at said operating site;

means normally blocking liquid flow through said tube means to said operating site;

means connected to said normally blocking means and responsive to a change in a characteristic of said pressure fluid in said tube means resulting from said actuation of said tool for automatically unblocking said tube means and supplying said liquid to said operating site;

a bypass valve manually actuable for applying gas pressure to said means normally blocking liquid flow to unblock same independent of tool actuation;

a first valve interposed between said pressure fluid source and said pressure fluid tube to said tool;

a second valve interposed between said pressure fluid source and said means normally blocking liquid flow;

a third valve interposed between said pressure fluid source and said means responsive to said change in character;

function selecting means manually settable to an automatic setting applying pressure fluid to unblock said first and second and third valves, for automatic supplying of liquid to said operating site upon actuating of said tool, said function selecting means being manually settable to a manual setting applying pressure fluid to unblock only said first and second valves and leave said third valve blocked, for precluding supplying of liquid to said operating site in response to actuation of said tool;

a fourth valve in series with said second valve and connecting the latter to said means normally blocking liquid a pressure fluid line connected to a point between said second and fourth valves, said pressure fluid line including said bypass valve in series with a shuttle valve and a pressure responsive operator for said fourth valve, said operator being responsive to supplying of pressure fluid thereto through said second valve and manually actuated bypass valve and shuttle valve for unblocking said fourth valve and thereby manually causing a flow of liquid to said operating site, said fourth valve also being energizable in the opposite direction through said shuttle valve by a line from said function selecting means in the automatic setting of the latter.

* * * * *

UNITED STATES PATENT OFFICE
CERTIFICATE OF CORRECTION

Patent No. 4,276,023           Dated   June 30, 1981

Inventor(s) Earl G. Phillips and Dee B. Ranger

It is certified that error appears in the above-identified patent and that said Letters Patent are hereby corrected as shown below:

Column 10, line 42;  change "fundtion" to ---function---.

Column 11, line  3;  delete "a".

Column 12, line 42;  change "as" to ---gas---.

Column 14, line 31;  after "liquid" insert ---flow;---.

Signed and Sealed this

Twenty-ninth Day of December 1981

|SEAL|

Attest:

GERALD J. MOSSINGHOFF

Attesting Officer        Commissioner of Patents and Trademarks